United States Patent [19]

Giannini et al.

[11] 4,174,299

[45] Nov. 13, 1979

[54] CATALYSTS FOR THE POLYMERIZATION OF OLEFINS

[75] Inventors: Umberto Giannini, Milan; Enrico Albizzati, Arona; Sandro Parodi, Oleggio; Franco Pirinoli, Milan, all of Italy

[73] Assignee: Montedison S.p.A., Milan, Italy

[21] Appl. No.: 919,495

[22] Filed: Jun. 27, 1978

Related U.S. Application Data

[63] Continuation of Ser. No. 707,018, Jul. 20, 1976, abandoned.

[30] Foreign Application Priority Data

Jul. 21, 1975 [IT] Italy .............................. 25588 A/75

[51] Int. Cl.$^2$ ........................... C08F 4/64; C08F 4/68
[52] U.S. Cl. ........................... 252/429 B; 252/428; 252/430; 252/431 R; 252/431 C; 252/431 N; 252/431 P; 526/139; 526/141; 526/142; 526/145; 526/125

[58] Field of Search ............... 252/429 B, 430, 431 R, 252/431 C, 431 N, 431 P, 428

[56] References Cited

U.S. PATENT DOCUMENTS

| 3,647,772 | 3/1972 | Kashiwa | 252/429 B X |
| 3,694,421 | 9/1972 | Vetter | 252/429 B X |
| 3,859,231 | 1/1975 | Kochhar et al. | 252/429 B X |

OTHER PUBLICATIONS

Lapporte et al., J. Org. Chem., 28 (Jul. 1963), pp. 1947–1948.

*Primary Examiner*—Patrick Garvin

[57] ABSTRACT

New catalysts for the polymerization and copolymerization of olefins are described. The catalysts are prepared from new components which are complexes of the metals Mg, Mn and/or Ca with the transition metals Ti, V and/or Zr, plus an electron-donor compound.

14 Claims, No Drawings

CATALYSTS FOR THE POLYMERIZATION OF OLEFINS

This is a continuation of application Ser. No. 707,018 filed July 20, 1976, now abandoned.

In our pending application Ser. No. 670,951, filed Mar. 26, 1976, we disclosed catalyst systems for polymerizing olefins and prepared from organometallic compounds of metals belonging to Groups I to III inclusive of the [Mendelyeev] Periodic Table and metal complexes having the general formula $$M_m M'_{2m} Y \cdot nE \quad (I)$$

in which
M = Mg, Mn and/or Ca;
m = a number from 0.5 to 2;
M' = Ti, V and/or Zr;
X = Cl, Br or I;
Y = one or more atoms or groups of atoms which are the same or different and selected from atoms of halogen; atoms of halogen and, contemporaneously, atoms of oxygen; —NR$_2$; —OR; SR;

$$-O-\overset{O}{\underset{\|}{C}}-R; \quad -O-\overset{O}{\underset{\underset{O}{\|}}{\overset{\|}{S}}}-R;$$

(in which R is a hydrocarbon radical, in particular an alkyl, aryl, cycloalkyl or aralkyl radical), acetylacetonate anion; acetylacetonate anion and, contemporaneously, oxygen atoms; said atoms or groups being present in such an amount as to satisfy the valence of M';
n = a number from 0.5 m to 20 m; and
E = an electron-donor compound selected from the following classes of compounds:
(a) esters of organic carboxylic acids;
(b) alcohols;
(c) ethers;
(d) amines;
(e) esters of carbonic acids;
(f) nitriles;
(g) phosphoramides, esters of phosphoric acid, and phosphorus oxychloride.

An object of this invention is to provide new catalysts which are highly active in the polymerization of olefins and, more particularly, in the polymerization of ethylene, alpha-olefins and mixtures of ethylene with alpha-olefins and/or with multi-olefins, including diolefins, and which are based on metal complexes different from those of formula (I) and which have the following general formula $$MM'TY \cdot nE \quad (II)$$

in which
M = Mg, Mn or Ca;
M' = Ti, V or Zr;
T = oxygen, the anion CO$_3''$, or a pair of monovalent groups selected from $$\begin{pmatrix}-OH,\\-OH\end{pmatrix} \begin{pmatrix}-OH,\\-Cl\end{pmatrix} \begin{pmatrix}-OR,\\-OR\end{pmatrix} \text{ and } \begin{pmatrix}-OR,\\-Cl\end{pmatrix}$$

in which R is an alkyl, cycloalkyl, aryl or alkylaryl radical containing from 1 to 20 carbon atoms;
Y = one or more atoms or groups, alike or different, and selected from halogen atoms, halogen atoms and, contemporaneously, oxygen atoms, —NR'$_2$, —OR', —SR', $$-O-\overset{O}{\underset{\|}{C}}-R', \quad -O-\overset{O}{\underset{\underset{O}{\|}}{\overset{\|}{S}}}-R',$$

(R' being a hydrocarbon radical, in particular an alkyl, aryl, cycloalkyl or aralkyl radical); acetylacetonate anion; acetylacetonate anion and, contemporaneously, oxygen atoms; such atoms or groups being present in such number as to satisfy the valence of M';
n = a number from 0.5 to 20; and
E = an electron-donor compound selected from
(a) esters of organic carboxylic acids;
(b) alcohols;
(c) ethers;
(d) amines;
(e) esters of carbonic acid;
(f) nitriles;
(g) esters of phosphoric and phosphorous acid; and
(h) phosphorus oxychloride.

The presently preferred electron-donor compounds E are alkyl esters of aliphatic or aromatic acids in which the alkyl radical contains from 1 to 8 carbon atoms, inclusive; ethers ROR' in which R and R', which may be the same or different, represent alkyl radicals containing from 1 to 8 carbon atoms, inclusive, aryl radicals, aromatic nitriles, or alkyl esters of phosphoric or phosphorous acid in which the alkyl contains from 1 to 8 carbon atoms, inclusive.

Typical preferred electron-donors include: ethyl acetate, ethyl benzoate, methanol, ethanol, ethyl ether, tetrahydrofuran, pyridine, ethylene carbonate, benzonitrile, and phosphorus oxychloride.

The complexes of the invention are prepared by reacting equimolar amounts of compounds MT and M'Y, in which M, T, M' and Y have the same significance as in formula (II), at a temperature from room temperature to 150° C., inclusive, in solvents E which are electron-donor compounds of one of the classes (a) to (g) disclosed hereinabove. The complexes found in the reaction can be isolated from the reaction mass by crystallization from the solvent E, by evaporation of the solvent, or by precipitation with a solvent in which the complexes are insoluble.

If either compound MT or compound M'Y is, or if both are, poorly soluble in solvent E, the reaction of those compounds can be carried out in an alternative electron-donor solvent E', in which at least one of those compounds is soluble, to obtain a complex MM'TY·nE' which, after isolation from the solvent E', can be treated at a temperature from room temperature to 150° C., inclusive, with an excess of a solvent E, which treatment shifts solvent E'. Such shifting of a solvent E' can also be accomplished by adding an excess of a solvent E to the solution of the complex MM'TY·nE' in solvent E'.

According to another embodiment of the invention, components which yield final catalysts of good activity in the polymerization of olefins can be obtained by reaction of the compounds MT and M'Y in a molar ratio other than 1:1. In this embodiment, the reaction product isolated by crystallization from the solvent, by evaporation of the solvent, or by precipitation of the reaction product with a suitable solvent, is a mixture which consists of the desired complex (or of such a complex comprising a solvent E') and a complex consisting of compound MT, or compound M'Y, and solvent E or solvent E'.

Compounds of Ti, V or Zr which can be used to prepare the metal complex (which is component (A) of the present catalysts) include: $TiCl_3$, $TiCl_4$, $TiOCl_2$, $TiBr_4$, $TiI_4$, $Cl_3TiOCH_3$, $Cl_2Ti(OC_4H_9)_2$, $Ti(OC_4H_9)_4$, $Cl_3TiN(C_6H_5)_2$, $Cl_3TiOCOC_6H_5$, $Cl_3TiSC_6H_5$, $Cl_3Ti$-acetylacetonate, $Cl_3TiOSO_2C_6H_5$, $Cl_3TiOC_6H_5$, $VCl_3$, $VCl_4$, $VOCl_3$, $Cl_2VOC_4H_9$, $V(OC_4H_9)_3$, $ClV(acetylacetonate)_2$, $Cl_2VOCOC_6H_5$, VO-acetylacetonate, $ZrCl_4$ and $Cl_3ZrOC_4H_9$.

Some examples of metal complexes comprised in general formula (II) are the following:
$MgTiOCl_4.2CH_3COOC_2H_5$
$MgTiOCl_3.4CH_3COOC_2H_5$
$MgTiOCl_3.5C_2H_5OH$
$MgTiCl_5OH.2CH_3COOC_2H_5$
$MgTi(OC_2H_5)_2(OCH_3)Cl_3.CH_3COOC_2H_5$
$MgTiCl_4(OC_2H_5)_2.CH_3COOC_2H_5$
$MgTiOCl_3.2(n-C_3H_7)_2O$
$MgTiOCl_3.5POCl_3$.

Organometallic compounds of the Groups I to III metals which are particularly suitable for use as component (B) of the present catalysts include: $Al(C_2H_5)_3$, $Al(C_2H_5)_2Cl$, $Al(i-C_4H_9)_3$, $Al(i-C_4H_9)_2Cl$, $Al_2(C_2H_5)_3Cl_3$, $Al(C_2H_5)_2H$, $Al(i-C_4H_9)_2H$, $Al(C_2H_5)_2Br$, $(C_2H_5)_2Al-O-Al(C_2H_5)_2$,

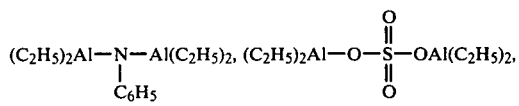

$LiAl(i-C_4H_9)_4$, $Li-i-C_4H_9$, and $Zn(C_4H_9)_2$.

The molar ratio between the organometallic compound and the complex containing Ti, V or Zr is not critical. For the (co)polymerization of ethylene and of alpha-olefins it is preferably comprised between 10 and 100.

The catalysts according to this invention are utilized in the (co)polymerization of olefins, in particular ethylene, propylene, butene-1 and 4-methylpentene-1, according to conventional techniques, i.e., in a liquid phase, in the presence or in the absence of an inert solvent, or in a gas phase. An aliphatic or cycloaliphatic hydrocarbon such as, for example, hexane, heptane, cyclohexane, may be used as the inert solvent.

The (co)polymerization temperature may range from −80° to 200° C., preferably from 50° to 100° C., operating at atmospheric pressure or under increased pressure. During (co)polymerization, the molecular weight of the polymer or copolymer can be regulated according to known methods, by operating, for instance, in the presence of alkyl halides, organometallic compounds of Zn or Cd, or hydrogen.

The following examples are given to illustrate the invention, and are not intended to be limiting.

EXAMPLE 1

2.02 g (50.1 m. moles) of MgO were suspended, in a nitrogen atmosphere, in 160 ml of anhydrous ethyl acetate. 5.57 ml (50.1 m. moles) of $TiCl_4$ were added dropwise and the whole was reacted for 3 hours at 40° C.; a yellow solution was obtained.

The reaction product was isolated by evaporation of the solvent and the resulting yellow powder exhibited, on analysis, a composition corresponding to formula $MgTiOCl_4.2CH_3COOC_2H_5$. The result obtained by polymerizing ethylene in contact with a final catalyst prepared from said complex and a component (B) is reported in the following Table, (Test I).

EXAMPLE 2

1.75 g (11.3 m. moles) of $TiCl_3HR$ ($H_2$-reduced $TiCl_4$) were dissolved, in a nitrogen atmosphere, in 250 ml of anhydrous ethyl acetate at 60° C. 0.46 g (11.3 m. moles) of MgO were added to the solution.

The reaction was allowed to proceed at 60° C. for 20 hours. A black solution was obtained and evaporated to dryness.

On analysis the resulting black powder had a composition of the formula $MgTiOCl_3.4CH_3COOC_2H_5$. The results obtained by polymerizing ethylene in contact with a final catalyst prepared from said complex and a component (B) are reported in the Table (Test II).

EXAMPLE 3

1.85 g (12 m. moles) of $TiCl_3$ were dissolved, in a nitrogen atmosphere, in 180 ml of anhydrous ethyl alcohol at 60° C. Subsequently, 0.484 g (12 m. moles) of MgO were added to the solution. The reaction was allowed to proceed at 60° C. for 8 hours. A brown solution comprising a brown powder in suspension was obtained. The suspension was evaporated to dryness and, on analysis, the brown powder was found to have a composition corresponding to the formula $MgTiOCl_3.5C_2H_5OH$.

Test III of the Table shows the results obtained by polymerizing ethylene in contact with a catalyst prepared from the complex.

EXAMPLE 4

1.88 g (24.4 m. moles) of HO—Mg—Cl were partially dissolved, in a nitrogen atmosphere, in 160 ml of anhydrous ethyl acetate at 60° C. 2.68 ml (24.4 m. moles) of $TiCl_4$ were added dropwise and the whole was reacted for 3 hours and 30 minutes. A yellow solution was obtained and evaporated to dryness. The yellow powder thus obtained was found, on analysis, to correspond to formula $MgTiCl_5OH.2CH_3COOC_2H_5$.

The results of polymerizing ethylene in contact with a catalyst prepared from said complex as one component thereof are reported in the Table (Test IV).

EXAMPLE 5

1.68 g (14.7 m. moles) of $Mg(OC_2H_5)_2$ were suspended, in a nitrogen atmosphere, in 100 ml of anhydrous ethyl acetate at 60° C.

A solution of 2.73 g (14.7 m. moles) of $Cl_3TiOCH_3$ in 50 ml of ethyl acetate was added dropwise to the suspension. The whole was reacted at 60° C. for 4 hours, thus obtaining a colorless solution.

The reaction product was isolated by evaporation of the solvent, and the resulting white powder revealed, on analysis, a composition corresponding to formula $MgTi(OC_2H_5)_2(OCH_3)Cl_3.CH_3COOC_2H_5$.

The ethylene polymerization test using that complex as catalyst component is reported in the Table (Test V).

EXAMPLE 6

3.6 g (33 m. moles) of Mg(OC$_2$H$_5$)$_2$ were suspended, in a nitrogen atmosphere, in 200 ml of anhydrous ethyl acetate at 60° C., and 3.6 ml (33 m. moles) of TiCl$_4$ were added dropwise thereto. After reaction at 60° C. for 4 hours, a light brown solution was obtained.

The reaction product was isolated by evaporation of the solvent, and the resulting brown powder exhibited, on analysis, a composition corresponding to formula MgTiCl$_4$(OC$_2$H$_5$)$_2$.CH$_3$COOC$_2$H$_5$. The results of polymerizing ethylene using such complex as catalyst component is reported in the Table (Test VI).

EXAMPLE 7

0.5 g of complex MgTiOCl$_3$.4CH$_3$COOC$_2$H$_5$ (prepared according to Example 2) was added to 20 ml of anhydrous dipropyl ether; the whole was reacted at 60° C. for 8 hours and a black solution was thus obtained.

The shift reaction was terminated by evaporation of CH$_3$COOC$_2$H$_5$, the resulting product being then isolated through evaporation of dipropyl ether.

A black powder was so obtained that, on analysis, revealed a composition corresponding to formula MgTiOCl$_3$.2(n-C$_3$H$_7$)$_2$O. The ethylene polymerization test carried out by using such complex as catalyst component is reported in the Table (Test VII).

EXAMPLE 8

1.2 g of complex MgTiOCl$_3$.4CH$_3$COOC$_2$H$_5$ (prepared according to Example 2) were added to 20 ml of phosphorus oxychloride; the whole was reacted at 60° C. for 8 hours, thus obtaining a green solution.

The shift reaction was terminated by evaporation of CH$_3$COOC$_2$H$_5$, and the product was successively isolated by evaporation of phosphorus oxychloride. A light brown powder was obtained that, on analysis, revealed a composition corresponding to formula MgTiOCl$_3$.5POCl$_3$.

The ethylene polymerization test conducted by using such complex as catalytic component is reported in the Table (Test VIII).

Ethylene Polymerization

A suitable amount of one of the catalytic complexes prepared in the foregoing examples and 1000 ml of deaerated anhydrous desulphurized n-heptane were introduced, along with 1 or 2 ml of Al(i-C$_4$H$_9$)$_3$, in a nitrogen atmosphere, into a stainless steel autoclave, having a 3-liter capacity, equipped with an anchor stirrer and heated to the desired temperature. Hydrogen and ethylene at prefixed partial pressures were added thereto, and the total pressure was kept constant throughout the polymerization by continuous feeding of ethylene.

After a 4-hour reaction, the polymerization was stopped, the reaction mass was filtered, and the resulting polymer was dried. The polymer inherent viscosity $\eta_{in}$ was determined in tetrahydronaphthalene at 135° C., employing concentrations of 0.25 g of polymer in 100 ml of solvent; the yield is expressed in grams of polymer obtained per gram of Ti.

The operating conditions and the results of the different tests are reported in the following table.

TABLE

| Test | Catalytic Complex Type | mg | Ti % | Al alkyl Al(i—C$_4$H$_9$)$_3$ ml. | Polymerization Ethylene atm | Hydrogen atm | Temp. °C. | Time Req. h | Polymer Product g | $\eta$ in dl/g | Yield Polymer/g of Ti |
|---|---|---|---|---|---|---|---|---|---|---|---|
| I | MgTiOCl$_4$ . 2CH$_3$COOC$_2$H$_5$ | 26 | 11.4 | 2 | 10 | 3 | 85 | 4 | 270 | 1.82 | 91,000 |
| II | MgTiOCl$_3$ . 4CH$_3$COOC$_2$H$_5$ | 50 | 13.2 | 1 | 10 | 3 | 100 | 4 | 420 | 2.10 | 63,500 |
| III | MgTiOCl$_3$ . 5C$_2$H$_5$OH | 47 | 10.9 | 1 | 10 | 3 | 95 | 4 | 280 | 1.95 | 55,000 |
| IV | MgTiCl$_5$OH . 2CH$_3$COOC$_2$H$_5$ | 17 | 11.05 | 2 | 10 | 3 | 85 | 4 | 320 | 2.05 | 170,000 |
| V | MgTi(OC$_2$H$_5$)$_2$(OCH$_3$)Cl$_3$ . CH$_3$COOC$_2$H$_5$ | 50 | 11.80 | 1 | 10 | 3 | 1(*) | 4 | 240 | 2.13 | 40,000 |
| VI | MgTiCl$_4$(OC$_2$H$_5$)$_2$ . CH$_3$COOC$_2$H$_5$ | 54 | 12.16 | 2 | 10 | 3 | 85 | 4 | 310 | 2.63 | 47,500 |
| VII | MgTiOCl$_3$ . 2CH$_3$CH$_2$CH$_2$OCH$_2$CH$_2$CH$_3$ | 47 | 11.9 | 2 | 10 | 3 | 100 | 4 | 170 | 1.90 | 30,000 |
| VIII | MgTiOCl$_3$ . 5POCl$_3$ | 49 | 5.50 | 2 | 10 | 3 | 95 |  | 210 | 2.05 | 77,000 |

We claim:

1. Components for catalysts useful in the polymerization of olefins, said components having the general formula MM'TY.nE in which
M = Mg, Mn or Ca;
M' = Ti, V or Zr;
T = oxygen, the anion CO$_3''$, or a pair of monovalent groups selected from the group consisting of

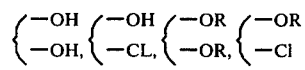

in which groups R is an alkyl, cycloalkyl, aryl or alkylaryl radical containing from 1 to 20 carbon atoms;
Y = halogen or halogen and alkoxy groups, said halogen or halogen and alkoxy groups being present in a number to satisfy the valence of the metal M';
n = a number from 0.5 to 20, inclusive; and
E = a hydrocarbyl electron donor compound selected from the group consisting of
(a) esters of organic carboxylic acids;
(b) ethers;
(c) amines;
(d) esters of carbonic acid;
(e) nitriles;
(f) esters of phosphoric or phosphorous acid; and
(g) phosphorus oxychloride.

2. Catalyst-forming components according to claim 1 in which, in the groups Y, R' is an alkyl, aryl, cycloalkyl or aralkyl radical.

3. A catalytic component according to claim 1, having the formula MgTiOCl$_4$.2CH$_3$COOC$_2$H$_5$.

4. A catalytic component according to claim 1, having the formula MgTiOCl$_3$.4CH$_3$COOC$_2$H$_5$.

5. A catalytic component according to claim 1, having the formula MgTiCl$_5$OH.2CH$_3$COOC$_2$H$_5$.

6. A catalytic component according to claim 1, having the formula MgTi(OC$_2$H$_5$)$_2$(OCH$_3$)Cl$_3$.CH$_3$COOC$_2$H$_5$.

7. A catalytic component according to claim 1, having the formula MgTiCl$_4$(OC$_2$H$_5$)$_2$.CH$_3$COOC$_2$H$_5$.

8. A catalytic component according to claim 1, having the formula MgTiOCl$_3$.2(n-C$_3$H$_7$)$_2$O.

9. A catalytic component according to claim 1, having the formula MgTiOCl$_3$.5POCl$_3$.

10. Components for catalysts useful in the polymerization of olefins, said components having the general formula MM'TY.nE in which
M = Mg, Mn or Ca;
M' = Ti, V or Zr;
T = oxygen, the anion CO$_3$″, or a pair of monovalent groups selected from the group consisting of

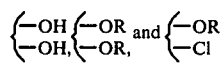

in which groups R is an alkyl, cycloalky, aryl or alkylaryl radical containing from 1 to 20 carbon atoms;
Y = halogen or halogen and alkoxy groups, said halogen or halogen and alkoxy groups being present in a number to satisfy the valence of the metal M';
n = a number from 0.5 to 20, inclusive; and
E = a hydrocarbyl electron donor compound consisting of an alcohol.

11. A catalytic component according to claim 10, having the formula MgTiOCL$_3$.5C$_2$H$_5$OH.

12. Process for preparing catalyst components having the general formula

MM'TY.nE in which
M = Mg, Mn or Ca;
M' = Ti, V or Zr;
T = oxygen, the anion CO$_3$″, or a pair of monovalent groups selected from the group consisting of

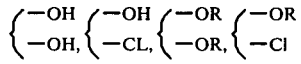

in which groups R is an alkyl, cycloalkyl, aryl or alkylaryl radical containing from 1 to 20 carbon atoms;
Y = halogen or halogen and alkoxy groups, said halogen or halogen and alkoxy groups being present in a number to satisfy the valence of the metal M';
n = a number from 0.5 to 20, inclusive; and
E = a hydrocarbyl electron donor compound selected from the group consisting of
(a) esters of organic carboxylic acids;
(b) ethers;
(c) amines;
(d) esters of carbonic acid;
(e) nitriles;
(f) esters of phosphoric or phosphorous acid; and
(g) phosphorus oxychloride;
said process being characterized in that a compound MT is reacted, at a temperature from room temperature to 150° C., inclusive, with a compound M'Y, in an MT/M'Y molar ratio of 1:1, in the selected electron-donor solvent E, and the resulting complex is isolated from said solvent by crystallization from the same solvent, by evaporation of said solvent, or by precipitation with a solvent in which the complex formed in the reaction is insoluble.

13. The process of claim 12, further characterized in that a compound MT is reacted, at a temperature from room temperature to 150° C., inclusive, with a compound M'Y in a suitable electron-donor solvent E' in which both of the compounds MT and M'Y are soluble, and subsequently an excess of the selected electron-donor solvent E is added to the complex MM'TY.nE' formed in the reaction before or after isolation thereof from the solution in solvent E'.

14. Catalysts for the (co)polymerization of olefins, prepared by mixing
(A) a catalyst-forming component having the general formula MM'TY.nE wherein
M = Mg, Mn or Ca;
M' = Ti, V or Zr;
T = oxygen, the anion CO$_3$″, or a pair of monovalent groups selected from the group consisting of

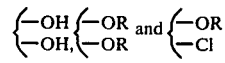

in which R is an alkyl, cycloalkyl, aryl or alkylaryl radical having from 1 to 20 carbon atoms;
Y = halogen or halogen and alkoxy groups, said halogen or halogen and alkoxy groups being present in such number as to satisfy the valency of M';
n = a number from 0.5 to 20, inclusive, and
E = a hydrocarbyl electron-donor compound selected from the group consisting of
(a) esters of organic carboxylic acids;
(b) alcohols;
(c) ethers;
(d) amines;
(e) esters of carbonic acid;
(f) nitriles;
(g) esters of phosphoric acid and phosphorus acid; and
(h) phosphorus oxychloride; with
(B) a catalyst-forming component which is an alkyl Al compound.

* * * * *